United States Patent
Snider et al.

(10) Patent No.: US 7,614,284 B2
(45) Date of Patent: Nov. 10, 2009

(54) OIL LIFE MONITORING SYSTEM FOR A DIESEL ENGINE

(75) Inventors: Matthew J. Snider, Howell, MI (US); David P. Quigley, Brighton, MI (US); Richard A. Barkman, Royal Oak, MI (US); Robert T. Stockwell, Ponca City, OK (US); Steven J. Andrasko, Wixom, MI (US)

(73) Assignee: GM Global Technology Operations, Inc., Detroit, MI (US)

( * ) Notice: Subject to any disclaimer, the term of this patent is extended or adjusted under 35 U.S.C. 154(b) by 261 days.

(21) Appl. No.: 11/650,866

(22) Filed: Jan. 8, 2007

(65) Prior Publication Data

US 2008/0163678 A1 Jul. 10, 2008

(51) Int. Cl.
*G01N 33/26* (2006.01)
(52) U.S. Cl. .................................... 73/53.05
(58) Field of Classification Search ........... 73/53.05, 73/10; 250/301
See application file for complete search history.

(56) References Cited

U.S. PATENT DOCUMENTS

| | | | |
|---|---|---|---|
| 5,169,785 A * | 12/1992 | Altman et al. ............... 436/60 |
| 6,327,900 B1 | 12/2001 | McDonald et al. |
| 6,952,951 B2 * | 10/2005 | Jakoby ..................... 73/53.05 |
| 2006/0005609 A1 * | 1/2006 | Blomkvist et al. ......... 73/53.05 |
| 2006/0207315 A1 * | 9/2006 | Niemann et al. ........... 73/53.05 |

* cited by examiner

*Primary Examiner*—Hezron Williams
*Assistant Examiner*—Alex Devito

(57) ABSTRACT

An oil life monitoring system for a diesel engine system includes a viscosity loss module, a viscosity gain module, and a remaining oil life module. The viscosity loss module determines a percentage of viscosity loss of engine oil based on fuel accumulation in the engine oil. The viscosity gain module determines a percentage of viscosity gain of engine oil based on fuel evaporation and/or soot accumulation in the engine oil. The remaining oil life module communicates with the viscosity loss module and the viscosity gain module and determines a percentage of oil life remaining based on the percentage of viscosity loss and/or the percentage of viscosity gain.

20 Claims, 3 Drawing Sheets

OIL LIFE MONITORING SYSTEM FOR A DIESEL ENGINE

FIELD OF THE INVENTION

The present invention relates to diesel engines, and more particularly to monitoring an oil life of diesel engines that use post injection regeneration of diesel particulate filters.

BACKGROUND OF THE INVENTION

Diesel engines have many moving parts that require lubrication. Engine durability is directly related to the ability of engine oil to lubricate the moving parts. However, the lubricating ability of the engine oil becomes degraded over time. Therefore, most manufacturers provide engine oil maintenance schedules to determine when the engine oil should be changed. The maintenance schedules are typically based on mileage although engine operating conditions directly relate to the degradation of engine oil. Thus, it is desirable to determine when the engine oil should be changed based on operating conditions of the engine.

In one method the degradation of engine oil is determined from monitoring engine revolutions, engine oil temperature, and soot accumulation in engine oil. However, during regeneration of a diesel particulate filter using a post injection strategy, fuel is accumulated in the engine oil. The accumulation of fuel degrades the ability of the engine oil to properly lubricate the engine. Therefore, it is desirable to determine when the engine oil should be changed due to the accumulation of fuel in the engine oil.

SUMMARY OF THE INVENTION

An oil life monitoring system for a diesel engine system according to the present invention includes a viscosity loss module, a viscosity gain module, and a remaining oil life module. The viscosity loss module determines a percentage of viscosity loss of engine oil based on fuel accumulation in the engine oil. The viscosity gain module determines a percentage of viscosity gain of engine oil based on fuel evaporation and/or soot accumulation in the engine oil. The remaining oil life module communicates with the viscosity loss module and the viscosity gain module and determines a percentage of oil life remaining based on the percentage of viscosity loss and/or the percentage of viscosity gain.

In other features of the invention, viscosity loss due to fuel accumulation in the engine oil, which occurs when the diesel engine system is regenerating a diesel particulate filter, is modeled. The viscosity loss module determines the percentage of viscosity loss based on a rate of viscosity loss. The rate of viscosity loss is based on a viscosity loss factor. The viscosity loss factor is based on an engine speed, an engine torque, a post injection fuel quantity, and a post injection time.

In still other features, viscosity gain due to fuel evaporation and/or soot accumulation, which occurs in engine oil when the diesel engine system is not regenerating a diesel particulate filter, is modeled. The viscosity gain module determines the percentage of viscosity gain based on a rate of viscosity gain. The rate of viscosity gain is based on a viscosity gain due to soot in engine oil and a viscosity gain due to engine oil temperature.

In yet other features, the remaining oil life module stores the percentage of oil life remaining in memory. If the percentage of oil life remaining is decreasing, the remaining oil life module displays the percentage of oil life remaining.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

Figure 1:
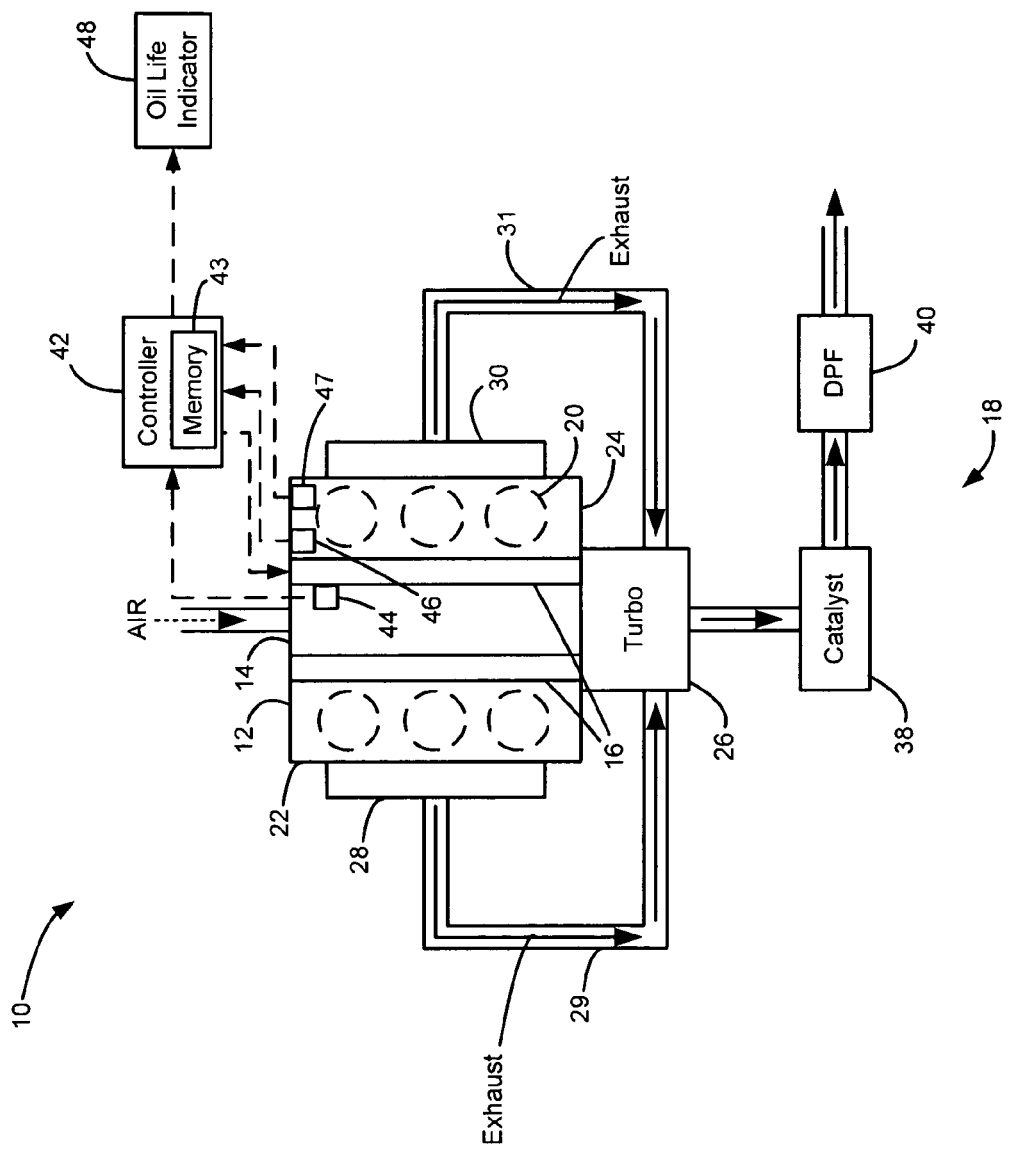
FIG. 1 is an exemplary diesel engine system that uses post-combustion injection to regenerate a diesel particulate filter.

The following description of the preferred embodiment(s) is merely exemplary in nature and is in no way intended to limit the invention, its application, or uses. For purposes of clarity, the same reference numbers will be used in the drawings to identify similar elements. As used herein, the term module refers to an application specific integrated circuit (ASIC), an electronic circuit, a processor (shared, dedicated, or group) and memory that execute one or more software or firmware programs, a combinational logic circuit, and/or other suitable components that provide the described functionality.

Referring now to FIG. 1, an exemplary diesel engine system 10 is illustrated. The diesel engine system 10 includes a diesel engine 12, an intake manifold 14, a fuel injection system 16, and an exhaust system 18. The exemplary engine 12 includes six cylinders 20 configured in adjacent cylinder banks 22,24 in V-type layout. Although FIG. 1 depicts six cylinders (N=6), it can be appreciated that the engine 12 may include additional or fewer cylinders 20. For example, engines having 2, 4, 5, 8, 10, 12 and 16 cylinders are contemplated.

Air is drawn into the cylinders 20 from the intake manifold 14 and is compressed therein. Fuel is injected into the cylinders 20 by the fuel injection system 16 and the heat of the compressed air ignites the air/fuel mixture. The exhaust gases are exhausted from the cylinders 20 and into the exhaust system 18. In some instances, the diesel engine system 10 can include a turbocharger 26 or a supercharger (not shown) that pumps additional air into the cylinders 20 for combustion with the fuel and air drawn in from the intake manifold 14.

The exhaust system 18 includes exhaust manifolds 28,30, exhaust conduits 29,31, a catalyst 38, and a diesel particulate filter (DPF) 40. First and second exhaust segments are defined by the first and second cylinder banks 22,24. The exhaust manifolds 28,30 direct the exhaust segments from the corresponding cylinder banks 22,24 into the exhaust conduits 29,31. The exhaust is then typically directed to drive the turbocharger 26. A combined exhaust stream flows from the turbocharger 26 through the catalyst 38 and the DPF 40. The DPF 40 filters particulates from the combined exhaust stream as it flows to the atmosphere.

A controller 42 that has memory 43 regulates operation of the diesel engine system 10 including DPF regeneration and an oil life monitoring system according to the present invention. More particularly, the controller 42 communicates with an intake manifold absolute pressure (MAP) sensor 44, an engine speed sensor 46, and an oil temperature sensor 47. The MAP sensor 44 generates a signal indicating the air pressure within the intake manifold 14. The engine speed sensor 46 generates a signal indicating engine speed (RPM). The oil temperature sensor 47 generates a temperature signal indicating temperature of the engine oil. Alternatively, a mathematical model may be used to generate the temperature signal. The controller 42 may determine an engine torque based on operating conditions of the diesel engine 12.

The controller 42 periodically estimates the amount of emitted particulates since the last DPF regeneration based on engine operating parameters. When the DPF 40 is deemed full of particulates, the controller 42 generates a regeneration signal and initiates DPF regeneration. During DPF regeneration, the controller 42 controls the fuel injection system 16 to inject fuel into the first and second cylinder banks 22, 24 at a calibrated time after combustion (i.e., post-combustion injection). Post-combustion injected fuel is expelled from the cylinders with the exhaust gas and is oxidized in the catalyst 38. Heat released during oxidation increases the exhaust gas temperature, which burns trapped soot particulates in the DPF 40.

The post-combustion injected fuel may accumulate in engine oil degrading the ability of the engine oil to lubricate the diesel engine system 10. Accordingly, the present invention monitors engine oil life based on the accumulation of fuel. The engine oil life may be displayed as a percent of remaining life on an oil life indicator 48.

Figure 2:
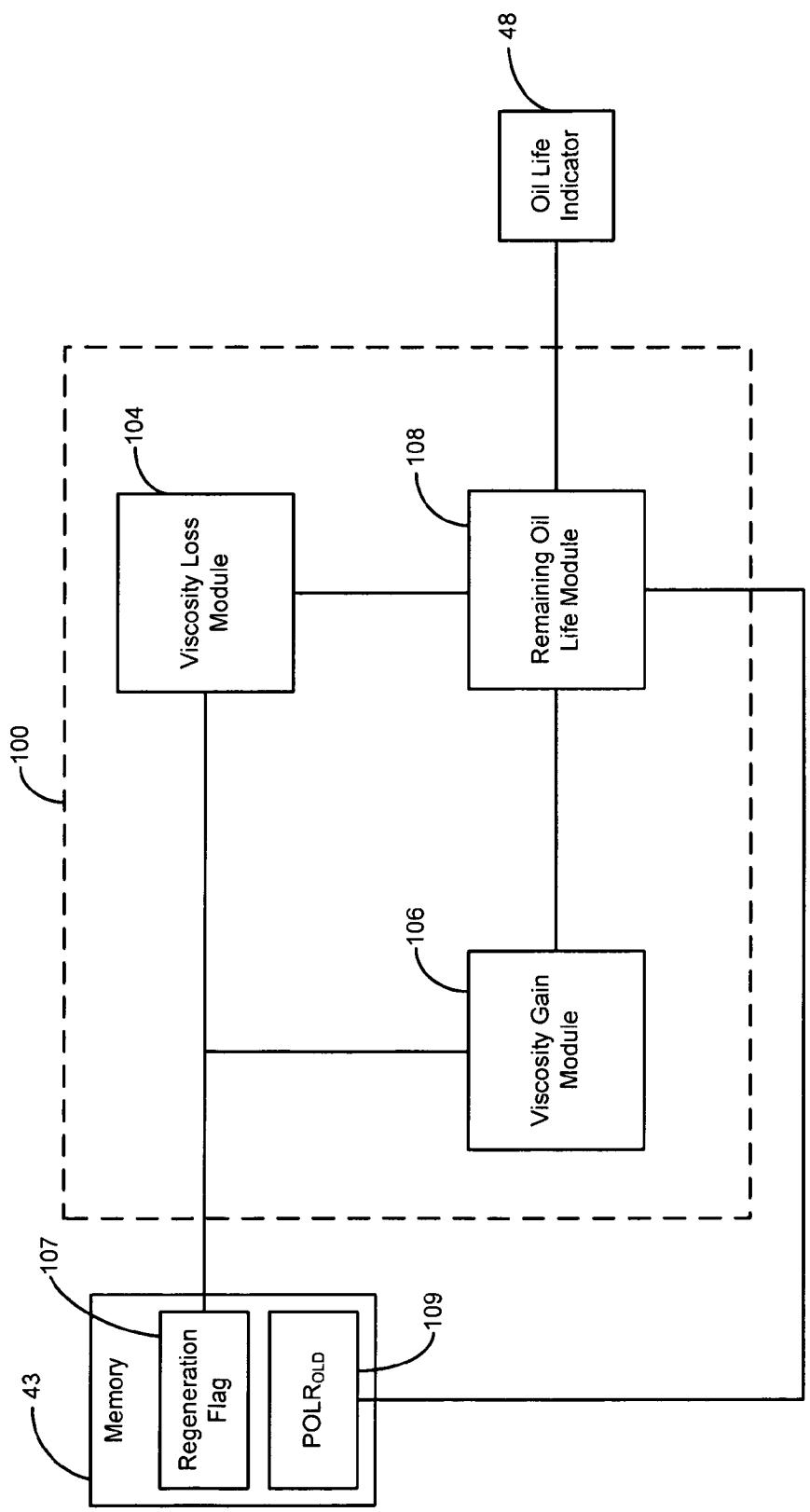
FIG. 2 is a functional block diagram of an oil life monitoring system according to the present invention.

Referring now to FIG. 2, an oil life monitoring system 100 includes a viscosity loss module 104, a viscosity gain module 106, and a remaining life module 108. When the controller 42 initiates DPF regeneration a regeneration flag 107 is set in memory 43.

When the diesel engine system 10 is regenerating the DPF 40, the viscosity loss module 104 determines a viscosity loss factor based on engine speed, engine torque, post injection fuel quantity, and post injection timing. The viscosity loss factor may be determined with the following equation:

$$V_{LF} = c_1 + c_2 E_s + c_3 E_T + c_4 Q_1 + c_5 Q_2 + c_6 T_1 + c_7 T_2$$

where $V_{LF}$ is the viscosity loss factor, $E_S$ is the engine speed, $E_T$ is the engine torque, $Q_1$ is a first post injection fuel quantity, $Q_2$ is a second post injection fuel quantity, $T_1$ is a first post injection timing, $T_2$ is a second post injection timing, and $c_1$-$c_7$ are constants that are experimentally determined.

Once the viscosity loss factor has been determined, the viscosity loss module 104 determines a viscosity loss rate. The viscosity loss rate represents viscosity loss per hour and may be determined from an experimentally determined lookup table.

The viscosity loss module 104 determines a percent viscosity loss based on the viscosity loss rate. The percent viscosity loss is independent of time and may be determined with the following equation:

$$V_{L\%} = \frac{V_{LR}}{t}$$

where $V_{L\%}$ is the percent viscosity loss, $V_{LR}$ is the viscosity loss rate, and t is a time that the diesel engine 12 has been operating according to the current operating conditions. For example, if the diesel engine 12 has been operating at 2000 RPM for 20 seconds, t would equal 20 seconds.

The remaining oil life module 108 uses the percent viscosity loss to determine a percent oil life remaining (POLR). More specifically, the remaining oil life module 108 retrieves a previously determined POLR from memory 43 and subtracts the percent viscosity loss to determine the POLR. The following equation may be used to determine the POLR:

$$POLR = POLR_{OLD} - V_{L\%}$$

where POLR is the percent oil life remaining, $POLR_{OLD}$ is the previously determined POLR, and $V_{L\%}$ is the percent viscosity loss. The POLR is stored in memory 43 as $POLR_{OLD}$ 109 and is used to calculate the POLR during the next cycle.

When regeneration of the DPF 40 is not occurring, the viscosity gain module 106 determines a viscosity gain due to soot accumulation in the engine oil and a viscosity gain due to oil temperature related fuel evaporation. Both the viscosity gain due to soot and viscosity gain due to temperature may be determined with a respective lookup table that is experimentally determined.

Once the viscosity gains due to soot and oil temperature have been determined, the viscosity gain module 106 determines a viscosity gain rate. The viscosity gain rate may be determined with the following equation:

$$V_{GR} = V_{GS} + V_{GT}$$

where $V_{GR}$ is the viscosity gain rate, $V_{GS}$ is the viscosity gain due to soot accumulation in the engine oil, and $V_{GT}$ is the viscosity gain due to engine oil temperature.

The viscosity gain module 106 determines a percent viscosity gain that is independent of time based on the viscosity gain rate. The percent viscosity gain may be determined with the following equation:

$$V_{G\%} = \frac{V_{GR}}{t}$$

where $V_{G\%}$ is the percent viscosity gain, $V_{GR}$ is the viscosity gain rate, and t is a time that the diesel engine 12 has been operating according to the current operating conditions.

The remaining oil life module 108 uses the percent viscosity gain to determine the POLR. More specifically, the remaining life oil module 108 retrieves the previously determined POLR from memory 43 and adds the percent viscosity gain to determine the POLR. The following equation may be used to determine the POLR when the viscosity is increasing due to fuel evaporation:

$$POLR = POLR_{OLD} + V_{G\%}$$

where POLR is the percent oil life remaining, $POLR_{OLD}$ is the previously determined POLR, and $V_{G\%}$ is the percent viscosity gain.

The POLR is stored in memory 43 as $POLR_{OLD}$ 109 and is used to calculate the POLR during the next cycle. However, the POLR is only displayed on the oil life indicator 48 when POLR is less than $POLR_{OLD}$ 109 to prevent a driver from observing an increase in the POLR.

Figure 3:
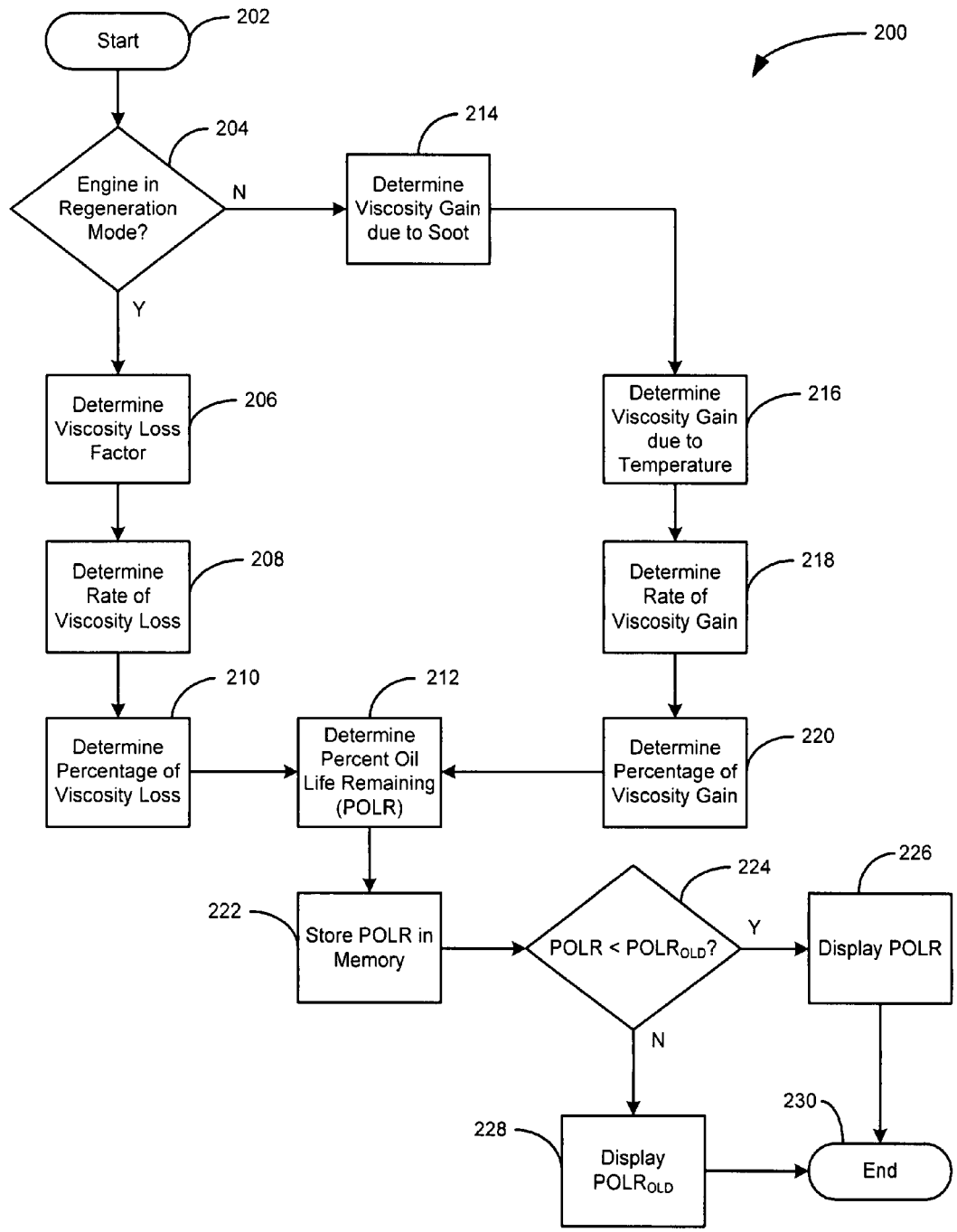
FIG. 3 is a flowchart illustrating exemplary steps taken by the oil life monitoring system of the present invention.

Referring now to FIG. 3, the oil life monitoring system 100 implements steps generally identified at 200. The process starts in step 202 when the diesel engine system 10 is started. In step 204, control determines whether the diesel engine system 10 is regenerating the DPF 40.

If the diesel engine system 10 is regenerating the DPF 40, the viscosity loss module 104 determines the viscosity loss factor in step 206. As previously discussed, the viscosity loss factor is based on engine speed, engine torque, post injection fuel quantity, and post injection timing. In step 208, the viscosity loss module 104 determines the viscosity loss rate based on the viscosity loss factor. As previously discussed, the viscosity loss rate represents viscosity loss per hour. In step 210, the viscosity loss module 104 determines the percent viscosity loss, which is independent of time, based on the viscosity loss rate.

The remaining oil life module 108 determines the POLR based on the percent viscosity loss in step 212. More specifically, the remaining oil life module 108 subtracts the percent viscosity loss from the POLR calculated during the last iteration.

If the diesel engine system 10 is not regenerating the DPF 40, the viscosity gain module 106 determines the viscosity gain due to soot accumulation in the engine oil in step 214. In step 216, the viscosity gain module 106 determines the viscosity gain due to engine oil temperature. The viscosity gain module 106 determines the rate of viscosity gain based on the viscosity gain due to soot accumulation in the engine oil and the viscosity gain due to engine oil temperature in step 218. As previously discussed, the viscosity gain represents viscosity gain per hour. In step 220, the viscosity gain module 106 determines the percent viscosity gain, which is independent of time, based on the viscosity gain rate.

The remaining oil life module 108 determines the POLR based on the percent viscosity gain in step 212. More specifically, the remaining oil life module 108 adds the percent viscosity gain to the $POLR_{OLD}$ 109, which is calculated during the last iteration.

The remaining oil life module 108 stores the POLR as $POLR_{OLD}$ 109 in memory 43 for the next iteration in step 222. In step 224, the remaining oil life module 108 compares the POLR to $POLR_{OLD}$ 109. If the POLR is less than the $POLR_{OLD}$ 109, the POLR is displayed on the oil life indicator 48 in step 226. If the POLR is not less than the $POLR_{OLD}$ 109, the $POLR_{OLD}$ 109 is displayed on the oil life indicator 48 in step 228. The process ends in step 230.

Those skilled in the art can now appreciate from the foregoing description that the broad teachings of the present invention can be implemented in a variety of forms. Therefore, while this invention has been described in connection with particular examples thereof, the true scope of the invention should not be so limited since other modifications will become apparent to the skilled practitioner upon a study of the drawings, the specification and the following claims.

What is claimed is:

1. An oil life monitoring system for a diesel engine system, comprising:
   a viscosity loss module that determines a percentage of viscosity loss of engine oil based on a post-combustion injection quantity and a post-combustion injection time wherein the post-combustion injection quantity is expelled during an exhaust stroke;
   a viscosity gain module that determines a percentage of viscosity gain of engine oil based on at least one of fuel evaporation and soot accumulation in said engine oil; and
   a remaining oil life module that communicates with said viscosity loss module and said viscosity gain module and that determines a percentage of oil life remaining based on at least one of said percentage of viscosity loss and said percentage of viscosity gain.

2. The oil life monitoring system of claim 1 wherein said viscosity loss occurs due to fuel accumulation caused by said post-combustion injection quantity and said post-combustion injection time when the diesel engine system is regenerating a diesel particulate filter.

3. The oil life monitoring system of claim 2 wherein said percentage of viscosity loss is based on a rate of viscosity loss.

4. The oil life monitoring system of claim 3 wherein said rate of viscosity loss is based on a viscosity loss factor.

5. The oil life monitoring system of claim 4 wherein said viscosity loss factor is based on an engine speed and an engine torque.

6. The oil life monitoring system of claim 1 wherein said viscosity gain occurs when the diesel engine system is not regenerating a diesel particulate filter.

7. The oil life monitoring system of claim 6 wherein said percentage of viscosity gain is based on a rate of viscosity gain.

8. The oil life monitoring system of claim 7 wherein said rate of viscosity gain is based on a viscosity gain due to soot in engine oil and a viscosity gain due to engine oil temperature.

9. The oil life monitoring system of claim 1 wherein said percentage of oil life remaining is stored in memory.

10. The oil life monitoring system of claim 1 wherein said remaining life oil module displays said percentage of oil life remaining when said percentage of oil life remaining is decreasing.

11. A method to monitor oil life of a diesel engine system, comprising:
    determining a percentage of viscosity loss of engine oil based on a post-combustion injection quantity and a post-combustion injection time wherein the post-combustion injection quantity is expelled during an exhaust stroke;
    determining a percentage of viscosity gain of engine oil based on at least one of fuel evaporation and soot accumulation in said engine oil; and
    determining a percentage of oil life remaining based on at least one of said percentage of viscosity loss and said percentage of viscosity gain.

12. The method of claim 11 wherein said viscosity loss occurs due to fuel accumulation caused by said post-combustion injection quantity and said post-combustion injection time when the diesel engine system is regenerating a diesel particulate filter.

13. The method of claim 12 further comprising determining said percentage of viscosity loss based on a rate of viscosity loss.

14. The method of claim 13 further comprising determining said rate of viscosity loss based on a viscosity loss factor.

15. The method of claim 14 further comprising determining said viscosity loss factor based on an engine speed and an engine torque.

16. The method of claim 11 wherein said viscosity gain occurs when the diesel engine system is not regenerating a diesel particulate filter.

17. The method of claim 16 further comprising determining said percentage of viscosity gain based on a rate of viscosity gain.

18. The method of claim 17 further comprising determining said rate of viscosity gain based on a viscosity gain due to soot in engine oil and a viscosity gain due to engine oil temperature.

19. The method of claim 11 further comprising storing said percentage of oil life remaining in memory.

20. The method of claim 11 further comprising displaying said percentage of oil life remaining when said percentage of oil life remaining is decreasing.

* * * * *